United States Patent [19]
Tiedemann

[11] Patent Number: 6,102,301
[45] Date of Patent: Aug. 15, 2000

[54] HUNTER'S RECONFIGUREABLE SCENT-HANDLING DEVICE

[76] Inventor: Larry E. Tiedemann, Rte. 1, Box 159, Winona, Minn. 55987

[21] Appl. No.: 09/404,647

[22] Filed: Sep. 24, 1999

[51] Int. Cl.⁷ ........................................... A61L 9/04
[52] U.S. Cl. ................................. 239/55; 220/916
[58] Field of Search .................. 239/36, 58, 60, 239/56, 55; 206/0.5, 0.7; 220/780, 796, 916, 799; 215/344, 345

[56] References Cited

U.S. PATENT DOCUMENTS

| | | | |
|---|---|---|---|
| 1,942,953 | 1/1934 | Bennett | 220/916 X |
| 2,111,985 | 3/1938 | Meyer | 220/916 X |
| 3,578,199 | 5/1971 | Duncan | 220/916 X |
| 3,799,118 | 3/1974 | Sandefur | 239/36 |
| 3,946,945 | 3/1976 | Odioso et al. | 239/58 |
| 4,078,686 | 3/1978 | Karesh | 220/916 X |
| 4,374,571 | 2/1983 | Hirvela | 206/0.5 |
| 4,609,245 | 9/1986 | Sakschek | 239/36 |

OTHER PUBLICATIONS

"Apple Land Sport" Product Catalog, p. 118, 1998, Gays Mills, WI 54631, Mike Pettit.

*Primary Examiner*—Kevin Weldon
*Attorney, Agent, or Firm*—Robert J. Harter

[57] ABSTRACT

A scent-handling device for attracting wild game includes a plug that snugly fits into either end of a receptacle to selectively place the scent-handling device in a sealed mode for tightly containing a scent inside the receptacle and a wide-open aerating mode for releasing the scent. The device includes several well thought out features that allow it to be inexpensively manufactured by way of a straightforward plastic injection molding process. A resilient clip extending sideways from the receptacle allows the clip and the receptacle to be injection molded together as a unitary piece without having to resort to a complicated mold having expensive side-action pulls. The clip includes several teeth that allow both the receptacle and the plug to be firmly fixed to various size branches or other items, thereby avoiding the problem of startling skittish animals with something dangling from the branch, or dangling while in transport. The plug includes an O-ring seal to create a piston/cylinder affect as the plug is inserted into the receptacle. Consequently, air forcibly escaping from the receptacle as the plug is being inserted produces a reassuring sound indicative of a tightly sealed closure.

17 Claims, 2 Drawing Sheets

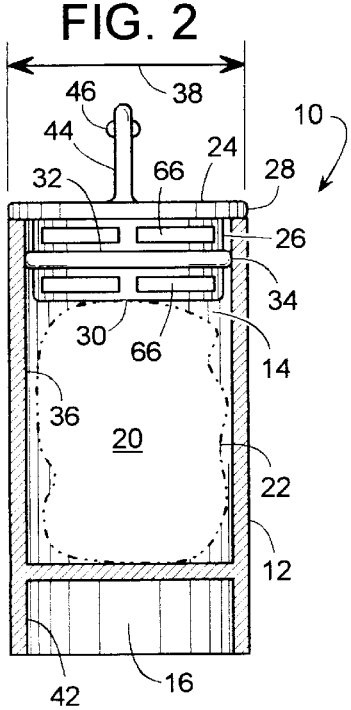
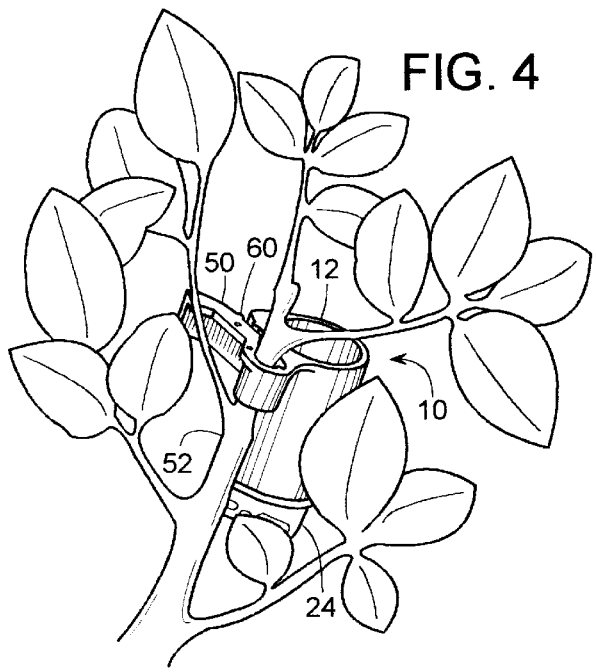
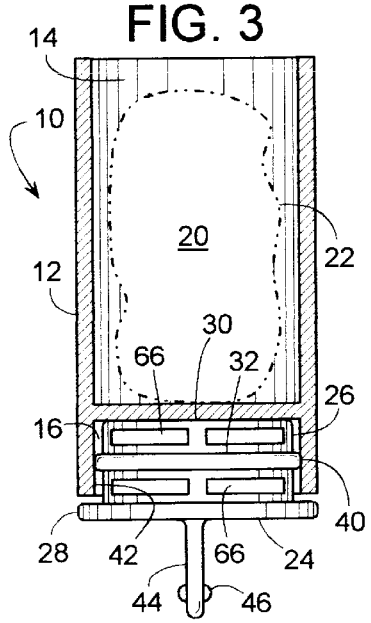
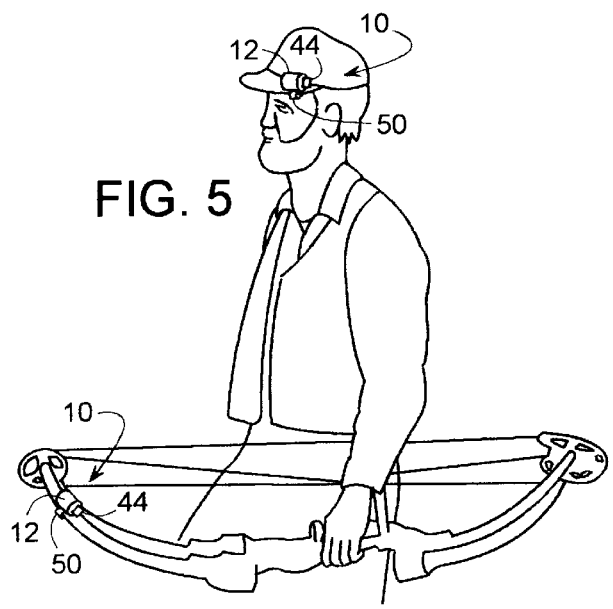

HUNTER'S RECONFIGUREABLE SCENT-HANDLING DEVICE

BACKGROUND OF THE INVENTION

1. Field of the Invention

The subject invention generally pertains to a scent handling device for wild game and more specifically to a scent-handling device that can be reconfigured between an operative aerating mode and a sealed mode.

2. Description of Related Art

Hunters often use scents when hunting deer, elk, bear, and various other big game. Currently, there are a wide variety of scents available for different animals and for affecting them in different ways. For example, cover scents are for covering or masking a hunter's natural odor that might otherwise alert an animal to danger. Food attractants, such as honey, apple, or corn; sexual attractants, such as estrus urine; and curiosity scents, such as grease, tend to attract an animal to within striking range of the hunter.

Scents are often in liquid form and are dispersed from a bottle directly onto trees, brush or on the ground itself in an area that would place an attracted animal in clear view of a hunter lying in wait. If no game is attracted to the scent within a reasonable period, the hunter may move on to another location, thus wasting any remaining scent left behind.

To avoid wasting scent, some hunters will dispense a scent into a container that is left on the ground or loosely hung from a tree branch or wire fence. Later, any unused scent (e.g., not yet evaporated) can be recovered by placing a cap on the container or by pouring the scent back into the scent's original dispenser. However, a couple of problems exist with such an approach.

First, when handling multiple containers or dispensers, as well as handling their caps, the liquid scent tends to get on the hunter himself Thus an animal may be drawn to the hunter rather than the hunter's chosen target location. If the animal approaches the hunter from behind, the hunter may never get a clear shot at the animal. Such a problem is especially common when the hunter is wearing gloves that may wick up the liquid scent or may reduce his dexterity for handling the small containers and caps. The problem is also common when there is no convenient place to store a container's cap, which may be covered with scent. If the cap is left loosely on the container, e.g., in a partially open position, the cap may inhibit the scent from freely escaping from the container by obstructing wind that may otherwise draw the scent from the container.

Second, when a scent container or its cap is loosely hung from a tree branch, skittish animals, such as deer, have been known to bolt off upon detecting loose items dangling from a tree.

SUMMARY OF THE INVENTION

To avoid the problems and limitations of current scent containers and dispensers, a primary object of the invention is to provide a scent-handling device that allows a hunter to avoid getting the scent on himself.

A second object is to provide a scent-handling device with a storage location for the device's cap.

A third object is to provide a simple scent-handling device that is readily manufactured by way of a plastic injection molding process that does not require any expensive side-action pulls or inserts.

A fourth object is to provide a somewhat rigid receptacle with a relatively soft O-ring seal that together provide a simple yet effective seal over a wide range of outdoor temperatures.

A fifth object is to provide a scent-handling device whose receptacle and seal are made of dissimilar materials, so that the seal material (e.g., buna-N) has appropriate sealing qualities, while the receptacle material is compatible with various scents such as urine and other animal wastes.

A sixth object is to provide scent-handling device comprising a receptacle, a plug and a cap with no loose, dangling parts regardless of whether it is in its operational aerating mode or while in its sealed mode during transport.

A seventh object is to provide a receptacle with a plug having a generally solid lower end to help displace air as well as any scent-related contents, such as cotton, that may be inside the receptacle.

A eighth object is to provide a plug that creates a piston/cylinder affect upon being inserted into a receptacle, whereby air forcibly escaping from the receptacle as the plug is being inserted produces a reassuring sound indicative of a tightly sealed closure.

A ninth object is to provide a clip with strategically arranged teeth to firmly grip branch-like elements of various diameter or thickness or firmly grip various other items including, but not limited to, a sling of a gun, a bow limb, or the brim of a cap.

A tenth object is to provide a tubular receptacle with an integral clip that extends generally perpendicular to a longitudinal centerline of the receptacle, so the receptacle and integral clip is readily manufactured by way of a plastic injection molding process that does not require any expensive side-action pulls or subsequent assembly.

An eleventh object is to provide a clip with a flange to add rigidity, so that the clip can be plastic injection molded of polypropylene which is a generally tough, resilient material that is suitable for use as a clip, but tends to warp if not properly designed with adequate reinforcement.

A twelfth object is to provide a plurality of scent-handling devices of similar construction but of a variety of colors, whereby the various contents of the scent-handling devices can be readily distinguished by way of a scent-handling device's particular color.

These and other objects of the invention are provided by a novel scent-handling device having a plug that fits either end of a receptacle to selectively place the scent-handling device in a sealed mode to contain a scent inside the receptacle and an operative, aerating mode to release the scent.

BRIEF DESCRIPTION OF THE DRAWINGS

FIG. 2 is a cross-sectional view taken along line 2—2 of FIG. 1 with the scent-handling device in a sealed mode.

FIG. 3 is the same as FIG. 2, but with the scent-handling device in an aerating mode.

FIG. 4 is a perspective view of a scent-handling device fixed to a branch and in its aerating mode.

FIG. 5 is a perspective view of a traveling hunter carrying two scent-handling devices in their sealed mode, with one scent-handling device being firmly clipped to the brim of the hunter's cap and the other one being firmly clipped the hunter's weapon.

DESCRIPTION OF THE PREFERRED EMBODIMENT

Figure 1:
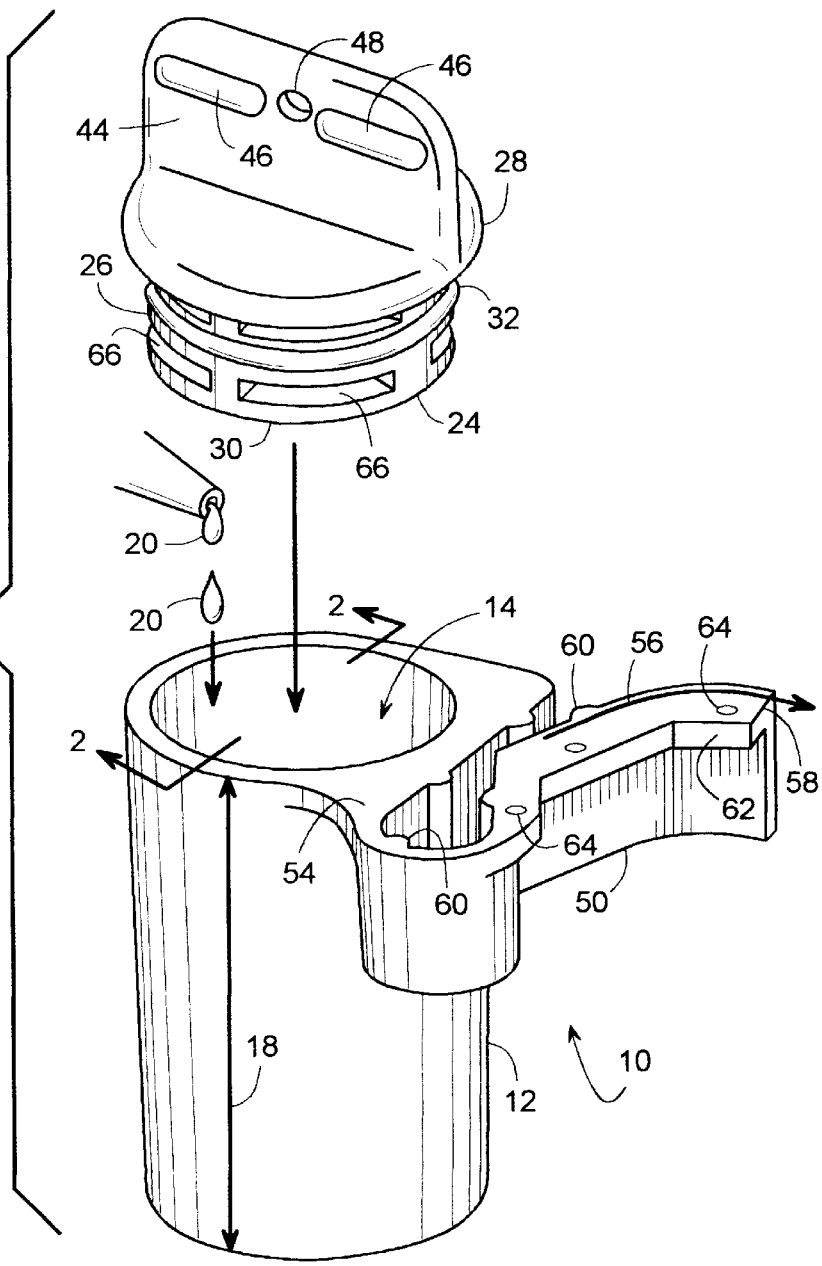
FIG. 1 is a perspective view of a scent-handling device with a plug being inserted into a primary cavity of a receptacle.

A scent-handling device 10, of FIGS. 1–4, includes a tubular (e.g., cylindrical, rectangular, irregular, multifaceted, etc.) receptacle 12 with a primary cavity 14 and a secondary cavity 16 at generally opposite ends of a length 18 of receptacle 12. Primary cavity 14 is adapted to contain a scent 20 that can be loosely deposited inside cavity 14 or preferably applied to a cotton ball 22 to inhibit scent 20 from dripping back out. Examples of scent 20 include, but are not limited to, cover scents; food attractants, such as honey, apple, or corn; sexual attractants, such as estrus urine; and curiosity scents, such as grease.

A plug 24 slips into primary cavity 14 or secondary cavity 16 to selectively and respectively place scent-handling device in a sealed mode (FIG. 2) and an operative aerating mode (FIG. 3). Plug 24 includes a shank 26 extending between a top flange 28 and a lower end 30 with an O-ring seal 32 interposed therebetween. In the sealed mode, O-ring 32 is adapted to provide a first press-fit 34 between an O-ring groove in shank 26 and an inner wall 36 of primary cavity 14. Press-fit 34 is in a radial direction generally perpendicular (with some allowance for plastic injection mold draft) to length 18 to sealingly hold plug 24 to primary cavity 14, thereby substantially sealing scent 20 inside. Lower end 30 serves as a standoff that helps keep any cotton or other scent-related materials from getting caught under O-ring 34. Lower end 30 also helps displace air from within primary cavity 14 when plug 24 is being inserted in the sealed mode. Top flange 28 has a flange width 38 that is appreciably larger than the inside diameter of primary cavity 14 to inhibit plug 24 from slipping entirely into cavity 14. In the aerating mode, O-ring 32 provides a second press-fit 40 against an inner wall 42 of secondary cavity 16 to hold plug 24 substantially fixed to receptacle 12. Plug 24 in this position allows scent 20 to escape substantially unrestricted from the wide-open primary cavity 14.

To ensure a positive, radial compressive seal, the outer diameter of O-ring 32 is slightly larger than the inside diameter of primary cavity 14. Moreover, lower end 30 is appreciably smaller in width or diameter than the inside diameter of cavities 14 and 16. This prevents shank 26 from interfering with the compression of O-ring 32, thus taking full advantage of the O-ring's ability to grip and/or seal against possible irregularities (e.g., warpage) of inner walls 36 and 42.

To ensure that plug 24 is firmly fixed to receptacle 12 in the aerating mode, the inside diameter of secondary cavity 16 is about the same as that of primary cavity 14. However, the seal between plug 24 and secondary cavity 16 is not as important. In some embodiments, for example, secondary cavity 16 may be provided with longitudinal slits that actually serve to ventilate or dry lower end 30 of plug 24 while in the aerating mode.

An integral pull-tab 44 protrudes from top flange 28 to allow a hunter to readily install or remove plug 24 from receptacle 12. In some embodiments, protrusions 46 are added to tab 44 to provide an even better grip. Also, tab 44 includes an optional eyelet 48 to attach a string, if desired.

A clip 50 integrally extends from receptacle 12 or plug 24, so that in its operational aerating mode device 10 can be forcibly clamped (i.e., fixed, as opposed to just hanging or dangling) to a branch-like element 52, such as a branch, fence wire, fence post, tree trunk, or any other elongated member of an indeterminate thickness or diameter. But equally important, the clamping feature also allows device 10 to be firmly attached to a variety of other items when device 10 is being transported while in its sealed mode (i.e., plug 24 in primary cavity 14), as shown in FIG. 5. Some examples of items to which device 10 could be clamped would include, but not be limited to, the sling of a firearm, a bow limb, or the brim of the hunter's cap. Thus, if there were ever any traces of scent on the exterior of device 10, the scent would be able to dry while the hunter is walking through the woods. Otherwise, the scent might wipe off on the interior of the hunter's pocket and subsequently attract an animal to the hunter himself, rather than to the intended location.

To this end, in some embodiments, clip 50 includes a proximal end 54 extending from a side-wall of receptacle 12 and lying along a path 56 that is generally perpendicular to length 18 of receptacle 12 to terminate at a distal end 58. Clip 50 has sufficient flexure and resilience to allow distal end 58 to bend away from receptacle 12, so that clip 50 can firmly clamp to branch-like elements of various thickness or diameter, or clamp to various other items as already mentioned. Clip 50 includes several spaced teeth 60 to further enhance its ability to grip, with different teeth being used for gripping the various-sized branch-like elements and other items of various sizes. A flange 62 lying generally perpendicular to length 18 provides clip 50 with optimum rigidity and resistance to warpage.

Scent-handling device 10 includes several well thought out features that allow it to be inexpensively manufactured by way of a straightforward plastic injection molding process. For example, clip 50 lying perpendicular to length 18 allows receptacle 12 and clip 50 to be plastic injection molded as a single unitary piece without having to resort to expensive side-action pulls on the mold. Integral flange 62 allows a relatively thin clip (desirable to minimize cycle time of the mold) to be made of a tough, resilient, chemical resistant, inexpensive polypropylene that, if not for flange 62, would have a significant tendency to wrap. Reverse-draft holes 64 allow mold pins to pull clip 50 out from its mold cavity. Providing one or more of holes 64 as a through hole allows a string to be threaded through it, if desired. Shank 26 is provided with several cross-cavities 66 that extend substantially perpendicular to length 18 (when plug 24 is inserted into cavity 14 or 16). This allows plug 24 to be injected as a unitary piece having a generally uniform wall thickness. Cross-cavities 66 allow plug 24 to be produced using a straight-pull mold having a parting line that lies generally parallel to pull-tab 44. Moreover, since both plug 24 and receptacle 12 can be produced by a simple, straight pull mold, both parts can be simultaneously injected in a single mold. Simply adding a conventional off-the-shelf O-ring then completes a finished product.

Although the invention is described with reference to a preferred embodiment, it should be appreciated by those skilled in the art that various modifications are well within the scope of the invention. For example, receptacle 12 and plug 24 can be of a variety of materials other than polypropylene. And O-ring 32 can be made of Buna-N or any one of a variety of other suitable materials. Moreover, for scent-handling devices of different colors, each color can serve as an indicator of a particular container's contents. Therefore, the scope of the invention is to be determined by reference to the claims that follow.

I claim:

1. A scent-handling device for use with a scent added thereto and being adapted to removably attach to an element of an indeterminate thickness, said scent handling device comprising:

a receptacle having a tubular shape defining a primary cavity and a secondary cavity, said tubular shape having a length extending from said primary cavity to said secondary cavity;

a plug adapted to selectively slip into said primary cavity and into said secondary cavity to selectively place said scent-handling device in a sealed mode and an aerating mode, respectively;

an O-ring softer than said plug and attached thereto, said O-ring being adapted to provide a first press-fit that sealingly holds said plug to said primary cavity to substantially seal said scent therein when said scent-handling device is in said sealed mode, and to provide a second press-fit that holds said plug to said secondary cavity to allow said scent to be released from said primary cavity when said scent-handling device is in said aerating mode; and a clip attached to at least one of said receptacle and said plug.

2. The scent-handling device of claim 1, wherein said clip is attached to said receptacle.

3. The scent-handling device of claim 2, wherein said clip integrally extends from said receptacle, whereby said receptacle and said clip comprise a unitary piece.

4. The scent-handling device of claim 2, wherein said clip includes a proximal end attached to said receptacle and a distal end adapted to move away from said receptacle, and wherein said clip extends from said proximal end to said distal end along a path that lies substantially perpendicular to a longitudinal direction defined by said length.

5. The scent-handling device of claim 4, wherein said clip includes a flange lying substantially perpendicular to said longitudinal direction.

6. The scent-handling device of claim 1, wherein said clip includes a plurality of teeth.

7. The scent-handling device of claim 1, wherein said first press-fit and said second press-fit are in a radial direction generally perpendicular to a longitudinal direction defined by said length.

8. The scent-handling device of claim 1, wherein said plug includes a top flange having a flange width that is appreciably larger than said primary cavity to inhibit said top flange from slipping entirely into said primary cavity, wherein said plug includes a lower end that is appreciably smaller than said primary cavity to allow said lower end to readily slip into said primary cavity, and wherein said O-ring is disposed between said top flange and said lower end, whereby said lower end tends to push any contents that may happen to be inside said primary receptacle away from said O-ring.

9. The scent-handling device of claim 8, further comprising a pull-tab protruding from said top flange, such that said top flange is interposed between said pull-tab and said lower end.

10. The scent-handling device of claim 8, wherein said plug includes a shank interposed between said top flange and said lower end, said shank defining a plurality of cross-cavities extending into said shank in a direction substantially perpendicular to said length when said scent-handling device is in said sealed mode.

11. A scent-handling device for use with a scent added thereto and being adapted to removably attach to an element of an indeterminate thickness, said scent handling device comprising:

a receptacle having a tubular shape defining a primary cavity and a secondary cavity, said tubular shape having a length extending from said primary cavity to said secondary cavity;

a plug adapted to selectively slip into said primary cavity and into said secondary cavity to selectively place said scent-handling device in a sealed mode and an aerating mode, respectively;

an O-ring softer than said plug and attached thereto, said O-ring being adapted to provide a first press-fit that sealingly holds said plug to said primary cavity to substantially seal said scent therein when said scent-handling device is in said sealed mode, and to provide a second press-fit that holds said plug to said secondary cavity to allow said scent to be released from said primary cavity when said scent-handling device is in said aerating mode;

a clip integrally extending from said receptacle such that said receptacle and said clip comprise a unitary piece, said clip having a proximal end attached to said receptacle and a distal end adapted to move away from said receptacle, said clip extending from said proximal end to said distal end alone a path that lies substantially perpendicular to a longitudinal direction defined by said length; and a flange disposed on said clip and lying substantially perpendicular to said longitudinal direction.

12. The scent-handling device of claim 11, wherein said clip includes a plurality of teeth.

13. The scent-handling device of claim 11, wherein said first press-fit and said second press-fit are in a radial direction generally perpendicular to said longitudinal direction.

14. The scent-handling device of claim 11, wherein said plug includes a top flange having a flange width that is appreciably larger than said primary cavity to inhibit said top flange from slipping entirely into said primary cavity, wherein said plug includes a lower end that is appreciably smaller than said primary cavity to allow said lower end to readily slip into said primary cavity, and wherein said O-ring is disposed between said top flange and said lower end, whereby said lower end tends to push any contents that may happen to be inside said primary receptacle away from said O-ring.

15. The scent-handling device of claim 14, further comprising a pull-tab protruding from said top flange, such that said top flange is interposed between said pull-tab and said lower end.

16. The scent-handling device of claim 15, wherein said plug includes a shank interposed between said top flange and said lower end, said shank defining a plurality of cross-cavities extending into said shank in a direction substantially perpendicular to said length when said scent-handling device is in said sealed mode.

17. A scent-handling device for use with a scent added thereto and being adapted to removably attach to an element of an indeterminate thickness, said scent handling device comprising:

a receptacle having a tubular shape defining a primary cavity and a secondary cavity, said tubular shape having a length extending from said primary cavity to said secondary cavity, wherein said length defines a longitudinal direction;

a plug adapted to selectively slip into said primary cavity and into said secondary cavity to selectively place said scent-handling device in a sealed mode and an aerating mode, respectively;

a top flange disposed on said plug and having a flange width that is appreciably larger than said primary cavity to inhibit said top flange from slipping entirely into said primary cavity;

a lower end disposed on said plug and being appreciably smaller than said primary cavity to allow said lower end to readily slip into said primary cavity;

a shank interposed between said top flange and said lower end of said plug, said shank defining a plurality of cross-cavities extending into said shank in a first direction substantially perpendicular to said longitudinal direction when said scent-handling device is in said sealed mode;

a pull-tab protruding from said top flange, such that said top flange is interposed between said pull-tab and said lower end;

an O-ring disposed about said shank and being softer than said plug, said O-ring being adapted to provide a first press-fit that sealingly holds said plug to said primary cavity to substantially seal said scent therein when said scent-handling device is in said sealed mode, and to provide a second press-fit that holds said plug to said secondary cavity to allow said scent to be released from said primary cavity when said scent-handling device is in said aerating mode, said first press-fit and said second press-fit being in a radial direction generally perpendicular to said longitudinal direction;

a clip integrally extending from said receptacle such that said receptacle and said clip comprise a unitary piece, said clip having a proximal end attached to said receptacle and a distal end adapted to move away from said receptacle, said clip extending from said proximal end to said distal end along a path that lies substantially perpendicular to said longitudinal direction;

a plurality of teeth disposed on said clip; and a flange disposed on said clip and lying substantially perpendicular to said longitudinal direction.

* * * * *